United States Patent
Pagliaro et al.

(10) Patent No.: US 6,797,773 B1
(45) Date of Patent: Sep. 28, 2004

(54) CATALYTIC MATERIALS FOR SELECTIVE OXIDATION OF ALCOHOLS, PROCESS FOR PRODUCTION THEREOF AND THEIR USE IN ALCOHOL OXIDATION PROCESS

(75) Inventors: Mario Pagliaro, Palermo (IT); David Avnir, Jerusalem (IL); Giulio Deganello, Palermo (IT); Jochanan Blum, Jerusalem (IL)

(73) Assignees: Consiglio Nazionale delle Ricerche, Rome (IT); Yissum Research Development Company of the Hebrew University of Jerusalem, Jerusalem (IL)

(*) Notice: Subject to any disclaimer, the term of this patent is extended or adjusted under 35 U.S.C. 154(b) by 0 days.

(21) Appl. No.: 09/646,346
(22) PCT Filed: Mar. 18, 1999
(86) PCT No.: PCT/IT99/00063
  § 371 (c)(1),
  (2), (4) Date: Nov. 15, 2000
(87) PCT Pub. No.: WO99/47258
  PCT Pub. Date: Sep. 23, 1999

(30) Foreign Application Priority Data

Mar. 18, 1998 (IT) .......................... RM98A0172

(51) Int. Cl.[7] .................. C08G 63/48; C08G 63/91
(52) U.S. Cl. .................... 525/50; 536/4.1; 536/18.5
(58) Field of Search ............... 525/50, 54.1; 536/4.1, 536/18.5

(56) References Cited

U.S. PATENT DOCUMENTS 5,292,801 A   3/1994   Avinar et al.

OTHER PUBLICATIONS

Matsui et al. Journal of Sol–Gel Science and Technology (1997), vol. 9, pp. 273–277.*

Shames, A. et al., "In situ EPR study of sol–gel processes", Journal of Non–crystalline solids, vol. 175, pp. 14–20, 1994.

Kazunori Matsui et al., "ESR Study of a Nitrooxide Radical in Sol–Gel Glasses", Journal of Sol–Gel Science and Technology, vol. 9, pp. 273–277, 1997.

Heeres, A. et al., "Synthesis of α– and B–D–Glucopyranuronate 1–Phosphate and α–D–Glucopyranuronate 1–Fluoride: Intermediates in the Synthesis of D–Glucuronic Acid from Starch", Carbohydrate Research, vol. 299, pp. 221–227, 1997.

* cited by examiner

Primary Examiner—James O. Wilson
Assistant Examiner—Patrick Lewis
(74) Attorney, Agent, or Firm—Browdy and Neimark, P.L.L.C.

(57) ABSTRACT

A versatile methodology to obtain efficient catalytic materials suitable for selective, liquid-phase oxidations of alcohols is described. Solid inorganic membranes were prepared by the sol-gel procedure by adding a solution of stable organic nitroxyl radicals at the onset of the polymerization of silicon alkoxide monomers. In this way, micro- and mesoporous materials can be obtained that axe effective and recyclable catalytic mediators for highly selective oxidations of a vast class of primary and secondary alcohols carried out with several primary oxidants. Delicate substrates such as carbohydrates and allylic alcohols can selectively be oxidized with these novel catalytic materials.

18 Claims, No Drawings

CATALYTIC MATERIALS FOR SELECTIVE OXIDATION OF ALCOHOLS, PROCESS FOR PRODUCTION THEREOF AND THEIR USE IN ALCOHOL OXIDATION PROCESS

CROSS REFERENCE TO RELATED APPLICATION

The present application is the national stage under 35 U.S.C. 371 of PCT/IT99/00063, filed Mar. 18, 1999.

BACKGROUND AND PREVIOUS KNOWLEDGE

Most (>90%) of the industrial chemical processes are catalytic [J. M. Thomas, W. J. Thomas, Principles and Practice of Heterogeneous Catalysis, VCFL Weinheim, 1997]. Of these, a percentage higher than 75% makes use of heterogeneous catalysts [J. H. Clark, Catalysis of organic Reactions by Supported Inorganic Reagents, VCH, Weinheim, 1994]. Heterogeneous catalysts are widely used in the petrochemical industry in several chemical processes including hydrocarbon cracking (on zeolites), olefin hydrogenations (on precious metals) and stereospecific polymerizations [J. H. Clark, Catalysis of Organic Reactions by Supported Inorganic Reagents, VCH, Weinheim, 1994]. On the other hand, many of the chemical synthesis of interest to the pharmaceutical and secondary chemical industries are liquid-phase homogeneous catalytic or stoichiometric processes [G. Sironi, La Chim. and l'Ind., 79 (1997) 1173–1177; M. Hudlicky oxidations in Organic Chemistry, Acs Monograph, No. 186, 1990]. The interest is high in converting homogeneous processes into efficient and clean heterogeneous catalytic conversions. The oxidation of alcohols to carbonyl derivatives is a typical fine chemical production process in need for such conversion [G. Sironi, La Chim. and l'Ind., 79 (1997) 1173–1177]. Due to the urgent demand of new oxidative technologies mentioned above, very recently Sheldon and colleagues were terming "philosophers' stones" efficient heterogeneous catalysts for liquid-phase oxidations in widely known international publication [R. A. Sheldon, m, Wallau, I. W. C. E. Arends, U. Schuchardt, Acc. Chem. Res., 31 (1998) 485–433]. Apart from industrial, large-scale high temperature (600° C.) catalytic dehydrogenations (equation 1) and oxidative dehydrogenations (equation 2) carried out on Ag and Cu catalysts [M. Muhler in: Handbook of Heterogeneous Catalysis, VCH, Weinheim, 1997],

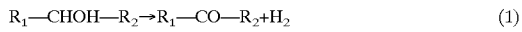

(1)

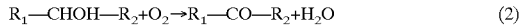

(2)

alcohol oxidations are carried out with stoichiometric amounts of oxidants (periodinanes, Dess-Martin reagent, chromium and manganese salts, mineral acids) or by electrochemical reactions. Environmental, economical and technological reasons make of primary importance the substitution of these homogeneous processes with heterogeneous catalytic oxidations carried out with clean oxidants such as $O_2$, $HO_2O_2$ or hypochlorite [J. A. Cusumano, J. Chem. Ed., 72 (1995) 959–964]. In general, however, the selectivity required in fine chemicals production is much higher as compared to that of classical large-scale heterogeneous catalysis.

Traditionally, heterogeneous catalysts are obtained by supporting the active species onto an inert solid of high surface area (silica, celite, carbon, alumina, clays etc.) in order to maximise the dispersion of the active species. The solid carrier can be an inorganic oxide or an organic polymer. Phase separation between the catalytic species and the reagents in the reaction mixture permits the facile separation of the catalyst and—in principle—either to reuse the catalyst in a subsequent reaction or its employment in a continuous process in which the reaction product is separated while the reactant is processed. Typically, heterogeneous catalysts ate prepared by impregnation of the inorganic support with a solution of the active species (i.e. metals ions) or by derivatising the surface of the solid in a heterogeneous reaction between the surface reactive groups (hydroxyl) and an organoderivate of the catalytic molecule.

Few mild catalytic oxidative processes are available. Catalysts of platinum and palladium supported on carbon are used at room temperature for alcohol oxidative dehydrogenation (equation 2) in batch reactors containing a suspension of the catalyst particles in a solution of the alcohol through which air is bubbled. The mild reaction conditions make it possible to oxidise sensitive compounds including carbohydrates [M. Besson, F. Lahmer, P. Gallezot, P. Fuertes, G. Flèche, J. Catal, 152 (1995) 116–122] and steroids, [T. Akihisa et al., Bull. Chem. Soc. Jpn. 59 (1986) 680–685), but reaction conditions need to be strictly controlled in order to avoid substrate overoxidation and rapid catalyst deactivation (by metal particles oxidation, sintering etc,). An efficient commercial oxidation catalyst is the inorganic oxide titanium silicalite (TS-1) used with aqueous $H_2O_2$ (30% w/w) for the catalytic oxidation of primary and secondary alcohols as described in [R. Murugawel. H. W. Roesky, Angew Chem. Int. Ed. Engl., 36 (1997) 477–479]. Selectivity of TS-1, however, is not high and different oxidisable groups such as double bonds and primary or secondary alcohol groups in a substrate are all rapidly oxidised as well.

There exists high demand of new, selective and efficient catalysts of oxidative processes and intense research efforts are devoted towards this aim both in industrial and in academic laboratories world-wide. Recently for instance, a new aerobic selective oxidative process has been described which uses diazo complexes of Cu (I) supported on $K_2CO_3$. Alcohols dissolved in apolar organic solvent can be dehydrogenated into carbonyl compounds by using oxygen contained in air as primary oxidant [I. E. Markó, P. R. Giles, M. Tsukazaki, S. M. Brown, C. J. Urch, Science, 274 (1996) 2044–2046]. Reactions temperatures employed are high (70–90° C.) and—due to low surface area of the inorganic support—an excess of $K_2CO_3$ (2 equiv.) is needed for optimum catalytic activity. The Authors therefore suggest the use of di-t-but-azodicarboxylate (DBAD) as a better primary oxidant affording less carbonate burden (10% equiv.) [I. E. Markó, P. R. Giles, M. Tsukazaki, S. M. Brown, C. J. Urch, Angew. Chem. Int. Ed. Engl., 36 (1997) 2208–2210]. Another novel catalytic reaction system has been introduced in Japan where alcohols are oxidised with 30% $H_2O_2$ in the presence of catalytic tungsten complexes with high turnover numbers [R. Nogori, K. Sato, M. Aoki, J. Takahi, J. Am. Chem. Soc., 119 (1997) 12386–12390].

Higly promising candidates suitable for the preparation of efficient heterogeneous catalysts may originate from stable organic nitroxyl radicals. These are di-tertiary-alkyl nitroxyl radicals (FIG. 1) with A representing a chain of two or three atoms (methylene groups) or a combination of one or two atoms with an oxygen or nitrogen atom as described in International patent application PCT/NL94/00217. Typically, the preferred radicals employed belong to the family of the 2,2,6,6-tetramethyl-1-piperidinyloxy (TEMPO, 1) and its derivatives substituted in position 4 (4-oxo-TEMPO, 2).

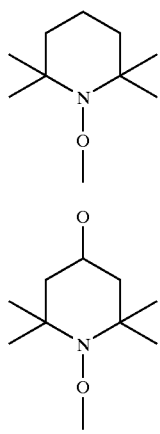

These species are highly efficient and versatile catalysts suitable for highly selective oxidation of hydroxyl containing compounds either to carbonyl or to carboxyl compounds, depending an applied reaction conditions. Their use as catalytic mediators in alcohol oxidations has been recently reviewed in depth in [A. E. J. de Nooy, A. C. Besemer, H. van Bekkum, Synthesis, (1996) 1153–1174]. Reactions can be carried our both at acidic and alkaline pH's with important difference in the selectivity observed. Furthermore, the oxidation reaction can be performed in different reaction media, i.e. in organic solvent, in biphasic water-organic solvent system and in water. In these catalytic oxidations, the active species (oxidant) is the (cyclic) nitrosonium ion which is generated in situ by adding an active primary oxidant including, among the others, Cu (II), NaOCl, NaOBr, NaBrO$_2$, N$_2$O$_4$, K$_3$Fe(CN)$_6$. It is believed that positive nitrogen of the cyclic nitrosonium ion attacks the alcoholic oxygen, with subsequent hydride abstraction in a bielectronic oxidative step involving carbonyl formation and acid release in the reaction mixture.

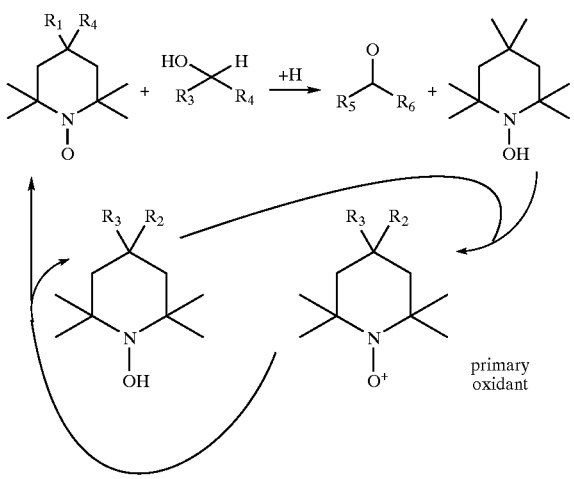

The hydroxylamine formed in the oxidative step disproportionates with the free radical to yield the nitrosonium ion or is directly oxidised with the primary oxidant to nitrosonium ion in a bielectronic reaction. As stated above, several alcoholic substrates can be oxidised at completion with high reaction rate and remarkable selectivity (compatibility with other oxidisable groups) and while alcohol oxidation in organic solvent stops at the first stage yielding a carbonyl compound, in H$_2$O the oxidation proceeds through a second oxidative step to yield a carboxylic acid.

In organic solvent containing up to 5% of H$_2$O air can be used as stoichiometric oxidant by adding a catalytic amount of Cu (I) so that, for instance, alcohols containing highly sensitive heterocyclic substitutes can be selectively oxidised (equation 6) into the corresponding carbonyl compound and no base has to be used to take up the acid formed in the oxidative step (equation 5), $$2Cu^+ + O_2 + 2H^+ \rightarrow 2Cu^{2+} + 2H_2O \qquad (3)$$

$$Cu^{2+} + TEMPO \rightarrow TEMPO + Cu^+ \qquad (4)$$

$$RCH_2OH + TEMPO^+ \rightarrow RCHO + H + TEMPO\text{-}OH \qquad (5)$$

$$RCH_2OH + 1/2O_2 \rightarrow RCHO + H_2O \qquad (6).$$

Remarkably, with the CuCl/O$_2$ system as primary oxidant, oxidation of allylic and benzylic alcohols proceeds smoothly even at −70° C. [M. F. Semmelhack, C. R. Shmid, D. A. Cortés, C. S. Chou, J. Am. Chem. Soc., 106 (1984) 3374–3376]. The simplicity and effectiveness of this molecular aerobic oxidation should be compared to Cu (I) mediated aerobic oxidations [L. Prati, N. Ravasio, M. Rossi, La Chim. and L'Ind., 79 (1997) 189–196]. In these latter reactions, including that recently developed by Zeneca [I. E. Markó, P. R. Giles, M. Tsukazaki, S. M. Brown, C. J. Urch, Science, 274 (1996) 2044–2046] or in enzymatic process recently developed [P. Chaudhuri, M. Hess, U. Flórke, K. Wieghardt, Angew. Chem., 110 (1998) 2340–2343], hydrogen transfer takes place between the alcoholic substrate and O$_2$, that are both completed to Cu (I) metal center. On the other hand, in TEMPO mediated oxidations, the oxidant is the cyclic nitrosonium ion and the only function of dissolved catalytic amount of Cu (I) is in forming the oxidant Cu (II) by splitting O$_2$ in a catalytic reaction cycle.

In the carbohydrate industry, oxidation is a useful means to obtain products of high added value starting from low cost, non toxic and readily available materials [K. van der Wiele, Carbohydrates in Europe, 13 (1995) 3]. Mono-oxidised sugars are the products of commercial interest but, due to the chemical similarity of different alcoholic groups in sugars, the selectivity of most chemical oxidants is low. Thus, often protection-deprotection steps of different oxidisable hydroxyls are required before and after the chemical oxidative step, as in the case of the commercial production of ascorbic acid (vitamin C) from a sorbose derivative. Accordingly, the introduction of new selective catalytic processes to substitute the traditional stoichiometric oxidations is the object of intense research efforts. New stable bimetallic (Pd—Bi/C) catalysts have been recently introduced for the preparation of mono-oxidised sugars; the catalyst Palatinose® (Pt/C) is used in an efficient, continuous catalytic process for the oxidation of D-glucose to D-gluconate. in which air is bubbled in an aqueous glucose solution and the reaction product is separated by electrophoresis while the sugar is continuously processed [M. Kunz et al., German patent DE OS 43 07 388 A1]

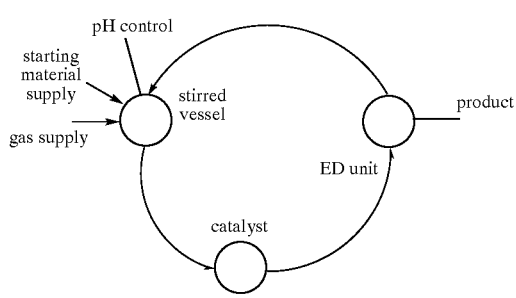

In contrast to D-gluconic acid, D-glucuronic acid is nor produced on an industrial scale despite its considerable importance [M. Boiret, A. Marty, J. Chem. Ed., 63 (1986) 1009–1011]. Its synthesis on a small scale is carried out with an enzyme and the price of the resulting compound is high. Moreover, native carbohydrate polymer containing carboxylic group at C-6 (polyuronates) find many commercial applications due to their remarkable properties as complexing agents and for abilities to form gels at low-concentrations (hyaluronanes, pectins, xanthan etc). A major breakthrough in the commercially relevant field of carbohydrate oxidations occurred therefore with the introduction of the regioselective homogeneous oxidation of carbohydrate primary alcohols into carboxylic acids mediated by nitroxyl radicals as described in PCT/NL94/00217. By using NaOBr as stoichiometric oxidant together with a catalytic amount of the radical 2,2,6,6-tetramethyl-1-piperidinyloxy (TEMPO) at alkaline pH (10) and low temperature (2° C.), sugars protected at the anomeric center are rapidly and selectively converted into respective uronates,

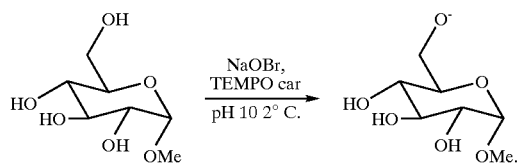

Due to a cyclic reaction mechanism, this alkaline oxidation method affords the rapid (80 min) regioselective primary alcohols oxidation of soluble polymeric carbohydrates (i.e. starch, inulin, pullulan) affording highly valuable and pure solution of the corresponding polyuronate. The use of NaOBr in place of NaOCl significantly increases the reaction rate. At pH 10 reaction rate is fastest while the non-selective oxidation of sugars by hypohalite has a much lower reaction rate and no side products are detected apart from the uronate. A recent comparative study clearly demonstrated the superiority of glucose oxidation mediated by TEMPO as compared to its oxidative dehydrogenation on Pt/C [K. Li, R. F. Helm, Carbohydr. Res., 273 (1995) 249–255]. Another comparative cost analysis comparing TEMPO (with CuCl/ air as stoichiometric oxidant) mediated oxidation with several stoichiometric oxidation protocols including the Swern's method (DMSO, oxalyl chloride) clearly supports the choice of the former as optimal method for fine alcohol oxidations [K, Dean Bowles, D. A. Quincy, J. I. McKenna, N. R. Natale, J. Chem, Ed., 63 (1986) 358–360]. The analysis took in consideration the expense of solvents and was based on 5 mol % as the amount of free radical needed for obtaining reasonable yields. A further advantage was found in the ease of upscaling of the method. It should be noted that the use of $O_2$ as the primary oxidant (and consequent formation of $H_2O$ as unique by-product) along with the low toxicity of the radicals are ideal intrinsic characteristics of the method from both environmental and safety viewpoints.

The versatility of alcohol oxidation mediated by nitroxyl radicals makes their use attractive to diverse industries. Accordingly, several homogeneous oxidative processes mediated by nitroxyl radicals have been patented and are commercially being used for the production of fine chemicals, including high yield (91.6%) E-retinol oxidation to E-retinal with $CuCl/O_2$ in DMF [G. H. Knaus, J. Paust, German.patent 3.705 785], the above mentioned alkaline regioselective oxidation of carbohydrate in water [PCT/NL94/00217], and the oxidation of alkyl polyglucosides (APG's) and several long chain alcohols (German patent DE 4209 869). Since nitroxyl radicals are costly (~10 S/g on a small scale, Aldrich catalogue 1999) and moderately toxic [T. S. Straub, J. Chem. Ed., 68 (1991) 1048–1049], their recovery would be desirable. Immobilization of the radicals on solid supports would facilitate their separation from the reaction mixture.

Few immobilization procedures have been reported and, with a single exception reported below, all concern organic polymers. A copolymerisation of an organic monomer containing a TEMPO precursor has been described in which the TEMPO precursor fragments are polymerised and then converted to TEMPO fragments [T. Miyazawa, T. Endo, M. Okawara, J. Polym. Sci., Polym. Chem. Ed., 23 (1985) 1527–1535]. Similarly, 4-amino-TEMPO has been immobilized on poly(acrylic acid) and the resulting polymer was subsequently coated on a glassy electrode [T. Osa et al., Chem. Lett., (1988) 1423–1428]. In the carbohydrate field, especially aiming at pharmaceutical and food applications, the preparation of heterogeneous catalysts of immobilisod nitroxyl radicals has been recently attempted. The reductive amination of the keto 4-oxo-TEMPO function by adding its solution in MeOH to a suspension of an amino-silica (Bio Sil NH2 90 15–35, Bio Rad), was followed by a reduction step with $NaBH_3CN$ as described in International patent application [PCT/NL96/00201]. As stated in the cited review it remains to be shown that the immobilized radicals are stable after frequent use and longer periods of time [A. E. J. de Nooy, A. C. Besemer, H. van Bekkum, Synthesis, (1996) 1153–1174]. Thus, for instance the catalytic activity of the material thereby obtained was tested in the oxidation of anomerically protected D-glucose; upon 3 consecutive un the material had lost its catalytic properties while reaction rate was considerably lower than corresponding homogenous reaction [A. Heeres, H. van Doren, K. F. Gotlieb, I. P. Bleeker, Carbohydr. Res., 299 (1997) 221–227]. The Authors concluded that azeotropic distillation is the method of choice for the recovery of TEMPO [PCT/NL96/00201].

DESCRIPTION OF THE INVENTION

The present invention describes the preparation of efficient and recyclable catalytic materials obtained supporting stable nitroxyl radicals in a solid, inert matrix by the sol-gel [C. F. Brinker, G. W. Scherer, Sol-gel Science, Academic Press, San Diego]. In fact the sol-gel technology allows to dope the glasses obtained through the polymerization (catalysed by acid or base) of metal alkoxides (or their hydrolysis products) in water with any kind of organic molecule by adding a solution of the doping substance at the onset of polymerization [D. Avnir, M. Ottrolenghi, S. Braun, R. Zusman, U.S. Pat. No. 5,292,801 (1994)]. The materials obtained in this way are porous glassy oxides with surface areas of up to hundreds of $m^2/g$ and narrow pores with diameters between 0.5 and 500 nm. The doped porous glasses show unique properties. Thus, i) the entrapped molecules retain their physical and chemical properties and, ii) are accessible to external reagents through the pore network. Moreover, iii) the inorganic matrix is chemically and thermally inert and iv) the entrapped molecules show enhanced stability [D. Avnir, D. Levy, R. Reisfeld, I Phys. Chem., 88 (1984) 5956–5959]. Because the sol-gel matrix is a high surface area absorbent which concentrates the reagents, often the reactions with the dopant have shown enhanced selectivity and sensitivity compared to the corresponding homogeneous reactions [O. Lev, M. Tsionski, L. Rabinovich, V. Glezer, S. Sampath, I. Pankratov, J. Gun, Anal. Chem., 67 (1995) 22A–30A].

In contrast with organic polymer supports, the ceramic sol gel supports are superior in their thermal stability, inertness towards the entrapped species, protectability of the entrapped molecule, and in their porosity and high surface area. Nitroxyl radical immobilization by the sol-gel method was carried out in order similarly to Lev [A. Shames, O. Lev, B. Iosefzon-Kuyavskaya, J. Non-Cryst. Solids 175 (1994) 14–20] and to [K. Matsui, T. Kaneko, Y. Yaginuma, M. Ryu, J. Sol-Gel Sci. Tech. 9 (1997) 273–277], both of which did not recognize the reactivity properties of the final doped xerogel. The cited [A. Heeres, H. van Doren, K. F. Gotlieb, I. P. Bleeker, Carbohydr. Res., 299 (1997) 221–227] surface derivarization procedure required several synthetic steps and resulted in a material whose catalytic activity deteriorated rapidly upon 3 consecutive oxidative runs. Indeed, we emphasize here the major difference between surface derivatization and entrapment in sol-gel materials: while the former requires the formation of a new covalent bond, and leaves the anchored molecule unprotected at the pore surface, the entrapment in sol-gel materials is physical in nature requiring no chemical step of covalent bonding, and highly protects the entrapped molecule within the surrounding cage of the ceramic material. An intermediate situation in which an amine function is for covalent bonding is added for anchoring the nitroxyl radical and for distributing it within the supporting matrix by the sol-gel procedure is also described and claimed below. Furthermore, we prepared mesoporous catalytic materials by i) coating the surface of an inorganic mesoporous inorganic oxide (e.g. pumice stones), and ii) by the preparation of areogels in place of above mentioned xerogels by removing the solvent under reduced pressure (15 mm Hg; liophilisation) as described in [N. Huesing, U. Schubert, Angew. Chem, Int. Ed. Engl., 37 (1998) 22–45].

The non-obvious novelty here is that when entrapped in a sol-gel glassy matrix, an active radical is not quenched but retains its characteristic oxidative properties. It is further non obvious that such entrapped oxidant exhibits high selectivity in alcohols oxidation as reported below; none of the doped catalysts leaches out while being accessible for reaction and that catalysts are recyclable. All of these properties are of major interest and relevance to the carbohydrate industry, and, in fact, to all industrial processes where an alcohol is to be oxidised. Porous silica sol-gel glasses were prepared which contain nitroxyl radicals both physically and chemically entrapped. Physical entrapment was carried out with TEMPO by adding the oxidant to the initial polymerizing mixture. Covalent entrapment was conducted by mixing 3-aminopropyl trimethoxysilane [$NH_2$—$CH_2CH_2CH_2$—Si$(OCH_3)_3$] with a solution of 4-oxo-TEMPO in methanol followed by reduction of the immune thereby formed. The precursor monomer is further polymerized with tetramethoxyorthosilicate (TMOS) according to the sol-gel procedure.

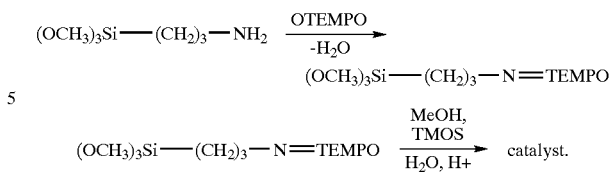

The polycondensation of alkoxysilanes is associated with gelation of the sol, which after drying is densified by mild heat treatment to form a porous glass. The properties of the final glass are determined by the chemical and physical conditions during the preparation process. They depend upon the ratio metal/water (r), the amount of added alcohol, the alkoxide, the pH, the type of the acid/bass catalyst, the temperature, the drying time and the amounts of added organic additives such as surfactants. Pore size and surface area are controlled by variations of all of these parameters. Hence, selection of optimal parameters is an important aspect of this invention. The following description of experiments are typical examples for such optimal procedures, but they are given without losing generality from the point of view of variations in these procedures which are obvious to the person skilled in the field.

EXAMPLES

Preparation of sol-gel glasses doped with nitroxyl radicals was conducted as follows.

Example 1

Sol-gel glasses physically doped with nitroxyl radical.

A standard mixture for the physical sol-gel glasses entrapment of TEMPO contained tetramethoxyorthosilicate (TMOS) (2.95 mL), $H_2O$ (1.0 mL) and MeOH (2 mL). The catalyst HCl ($10^3$ M, 1.0 mL) and 50 mg TEMPO, dissolved in methanol (2 mL), were added to the hydrolyzed TMOS solution. Gelation took place after approximately 2 hours in glass vessels covered with an aluminum foil and the gels were then aged for 4 days at ambient temperature. Final drying was affected in an incubator oven at 50° C. for 6 days, reaching constant weight This procedure yields glasses doped with TEMPO in any desired shape and form (discs, rods, granules, powders, films etc.). The procedure described yielded a monolithic glass which was crushed in granules.

Example 2

Sol-gel glasses chemically doped with nitroxyl radical.

The chemical entrapment of the nitroxyl radicals was carried out in 2 steps. The catalyst is prepared by anchoring the nitroxyl radical through the oxo group of 4-oxo-TEMPO to the amino group of aminopropyltrimethoxysilane and further polymerizing the as resulting monomer with an acidic sol of tetramethoxyorthosilicate (TMOS,Si$(OCH_3)_4$). After 24 h stirring a solution of 4-oxo-TEMPO (424 mg) in methanol (3 mL) with aminopropyltrimethoxysilane ($H_2N$—$(CH_2)_3$—Si$(OCH_3)_3$, 480 mL, 10% molar excess) the resulting alcoholic immine is mixed with a portion of acidic sol stock TMOS solution previously prepared by mixing TMOS (29,5 mL), $H_2O$ (3.6 mL), MeOH (32,40 mL) and HCl lN (140 $\mu$l). Thus, a portion of the sol stock mixture (3.28 mL) was partially neutralized with $NH_4OH$ 0.1 M (69.8 $\mu$L) and mixed together with 1.14 mL of the immine precursor solution. Methanol (7.41 mL) was subsequently added under stirring followed by H$_2$O (3.88 mL) to promote hydrolysis and condensation. As a formal acidity measure, pH (6.0) refers to the concentration of hydrogen ions in the total volume. The resulting mixture (Si:H$_2$O:MeOH= 1:5.5:6) gelled rapidly (10 min) in a transparent, elastic alcogel coloured in orange which was left at ambient temperature for 3 days and subsequently dried at 50° C. resulting in a monolithic doped xerogel of 0.93 g. The sol described above was dried by removing the solvent under reduced pressure (15 mm Hg) affording an orange areogel powder.

Example 3

Chemical Entrapment.

Sol-gel glasses doped with OTEMPO.

The chemical entrapment of the nitroxyl radicals is carried out in two stages.

Usually, a sol stock solution contains TMOS, MeOH, H$_2$O and HCl, remaining stable for months. Thereafter, a solution containing a chemically bound TEMPO precursor is prepared.

An OTEMPO solution is stirred in methanol with tri-amino-propyl tri-methoxy-silane (for 2 hours at 20° C.). Typically, 4 ml of the sol stock solution containing TMOS, MeOH, H$_2$O and HCl (7×10$^{-5}$ molar) with a molar ratio of 1:5:4:1:7×10$^{-4}$ (J. Brinker's procedure, Sandia, Sandia National Labs, US) are added with a 60 mg OTEMPO solution in methanol (2.45 ml) and tri-amino-propyl tri-methoxy-silane (1.64 ml) with a subsequent adding of H$_2$O (1.7 ml). Gelification occurs in a few minutes. Then the gel is dried in an incubator at 50° C. covered with a tinfoil. The resulting xerogel (dried gel) contains nitroxyl radicals that are chemically bound to the silica matrix by an immine group that can be easily reduced with NaBH$_3$CN. As in the previous procedure, in this case as well the glasses can be obtained in any desired shape.

In the oxidative procedure the oxidized substrate is isolated, while the nitroxyl radical is recovered and recycled, thanks to the catalyst heterogenous nature.

Example 4

Mesoporous inorganic carriers coated with Sol-gel doped films.

The sol described above in Examples 2 and 3 containing nitroxyl radicals chemically linked was used to coat the surface of an inorganic mesoporous inorganic oxide (pumice stones from the Lipari island (Italy)) leaving the sol in contact with the support for about 5 hours and removing the solvent under reduced pressure (15 mm Hg) as described in International patent application PCT 0 832 561 AZ.

Example 5

Catalytic activity in the nitroxyl radicals entrapped in sol gel glasses.

Typical procedure:

The reactions of catalytic oxidation are carried out adding granules of the doped materials (e.g. 0.247 g of a catalyst 3.70% (w/w) in TEMPO, or 0.352 g of a catalyst 3.24% (w/w) in 4-oxo-TEMPO) to an aqueous solution of methyl-α-D-glucopyranoside (MGF, 1.0 g and 0.10 g of sodium bromide in 200 mL H$_2$O at 4° C. A cold hypochlorite solution (10 mL, 10% w/w) previously brought to pH 10 by Adding 4M HCl is then added at once. The pH is followed and kept costant at 10 by adding 0.5M NaOH to the mixture reaction in order to neutralize the acid released during the reaction (Diagram I). When the oxidation is completed (no more acid formation, typically 40 min) the reaction mixture is quenched by adding 96% ethanol (4 mL) and by changing the pH to 6 by addition of 4M HCl. The catalyst is filtered, and the product, sodium methyl-α-D-gluco-pyranoside uronate is obtained from the filtrate by freeze-drying in a lyophylizer. The yield of the reaction is practically quantitative. For the next reaction cycle, the catalyst is washed with cold water and reused as such under the same conditions described above.

Example 6

The catalytic activity of the sol-gel materials doped with nitroxyl radical thus far described was tested in different oxidative runs using α-D-methylglucopyranoside and trans-cinnamyl alcohol as substrates along with aqueous hypobromite and CuCl/air as primary oxidants, respectively. In a typical sugar oxidation they catalytic oxidation reaction was carried out by adding granules of the doped materials (e.g. 0.247 g of a catalyst 3.70% (w/w) in TEMPO, or 0.352 g of a catalyst 3.24% (w/w) in 4-oxo-TEMPO) to an aqueous, solution of methyl-α-D-glucopyranoside (MGP, 1.0 g) and sodium bromide (0.10 g) in 200 mL H$_2$O at 4° C. A cold hypochlorite solution (10 mL, 10% w/w) previously brought to pH 10 by adding 4M HCl, was then added at once. The pH was kept constant at 10 by adding 0.5M NaOH in order to neutralize the acid released during the reaction. When the oxidation was completed (no more acid formation, typically 40 min), the reaction mixture was quenched by adding 96% ethanol (4 mL) and by changing the pH to 6 by addition of 4M HCl. The catalyst was filtered, and the product (sodium methyl-α-D-glucopyranosideuronate) was obtained from the filtrate by freeze-drying in a lyophylizer. The yield of the reaction was practically quantitative. For the next reaction cycle, the catalyst was washed with cold water and reused as such under the same conditions described above. The catalyst was reused in 3 subsequent similar oxidation runs of the same substrate MGP with minor decrease in activity. The elemental analysis after oxidative runs did not detect any nitrogen, thus establishing the lack of leaching of the entrapped nitroxyl radicals in the reaction solution.

Example 7

Leaching, recyclability and selectivity.

The catalyst is reused in 5 subsequent similar oxidation runs of the same substrate MGP with no decrease in yield or activity.

The spectra NMR cannot detect any secondary product, with the exception of the desired sodium methyl-α-D-glucopyranoside uronate. The elemental analysis after each of the four consecutive oxidative runs does not detect any nitrogen, thus establishing the lack of leaching of the nitroxyl radicals entrapped in the reaction solution. It is interesting that no induction time whatsoever is observed in the subsequent oxidation runs carried out in the heterogeneous oxidation system, compared to the 15 minutes in the corresponding homogenous reaction carried out with the TEMPO solution.

What is claimed is:

1. A reactive sol-gel catalytic porous material comprising a mesoporous inorganic support and a sol-gel catalytic porous material coated on said mesoporous inorganic support, said sol-gel porous material comprising a copolymer of a) 3-amino-propyl-trimethyloxysilane as a monomer precursor and b) a dopant consisting of 4-oxy-2,2,6,6-tetramethyl-1-piperidinyloxy as a stable nitroxyl radical or as a precursor thereof tethered to said monomer precursor through reductive amination, and c) at least one additive selected from those known to be useful in the preparation of porous materials to form a gel containing said dopant trapped therein.

2. A process for the preparation of a reactive sol-gel catalytic porous material comprising chemically doping said material with stable organic nitroxyl radicals, by carrying out the steps of:

copolymerizing a solution including:

a) 3-amino-propyl-trimethoxysilane as a monomer precursor;

b) a dopant consisting of 4-oxy-TEMPO as a stable nitroxyl radical or a compound that forms 2,2,6,6-tetramethyl-1-piperidinyloxy under the instant reaction conditions;

c) a solvent including $H_2O$ and a co-solvent selected from the aliphatic alcohols; an acid or base to catalyze the processes of sol-gel hydrolysis and copolymerization; and one or more additives selected from those known to be useful in the preparation of porous materials to form a gel containing said dopant trapped therein;

d) tethering said radical to said monomer precursor through reductive amination, said solution including $H_2O$ as a solvent and a co-solvent from the aliphatic alcohols; an acid or base to catalyze the processes of sol-gel hydrolysis and copolymerization; and one or more additives selected from those known to be useful in the preparation of porous materials to form a gel containing said dopant chemically trapped therein;

e) evaporating said solvent;

f) drying said gel; and g) coating said gel on a mesoporous inorganic support.

3. A process for a liquid-phase oxidative conversion of a substrate of a primary or secondary alcohol into a carbonyl or carboxyl derivative thereof, comprising said conversion being carried out with said substrate in catalytic presence of a reactive sol-gel catalytic porous material either chemically or physically doped with stable organic nitroxyl radicals, said material being coated on a mesoporous inorganic support and containing a copolymer of a) at least one monomer precursor selected from the group consisting of metal and semi-metal alkoxides, metal esters and semi-metal esters, of the general formula

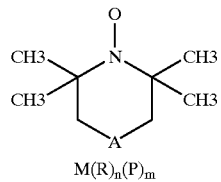

$M(R)_n(P)_m$ wherein M is a metal or a semimetal, R is an hydrolyzable substituent, P is a non-hydrolyzable group, n is an integer of 1 to 6, and m is an integer of 0 to 6, and b) a dopant consisting of a stable di-tertiary-alkyl nitroxyl radical or a precursor thereof of the formula, wherein A represents a chain of two or three carbon atoms, one or two of said carbon atoms being eventually substituted by one oxygen or nitrogen atom, and one or more additives selected from those known to be useful in the preparation of porous materials to form a gel containing said dopant trapped therein.

4. A process for liquid-phase oxidative conversion of a substrate of a primary or secondary alcohol into a carbonyl or carboxyl derivative thereof, comprising conducting said oxidative conversion in the presence of a doped catalytic material according to claim 2, and in the presence of a primary oxidant effected in selective alcohol oxidations mediated by nitroxyl radicals.

5. The process according to claim 3, wherein said non-hydrolyzable group is H, an alkyl, aryl or fluoroalkyl group or an aminoalkyl group.

6. The process according to claim 2, wherein said step (f) of drying the gel is a liophilisation carried out at a pressure lower than 70 mm Hg, to obtain a mesoporous aerogel powder.

7. The process according to claim 2, wherein said step (f) of drying the gel is a mild heat treatment carried out at an atmospheric pressure and a temperature no greater than 100° C.

8. The process according to claim 2, wherein said nitroxyl radical is added to said solution along with said monomer precursor in a one-step procedure.

9. The process according to claim 2, wherein in a two-step procedure, first said compound that forms 2,2,6,6-tetramethyl-1-piperidinyloxy under the instant reaction conditions is hydrolyzed in part with water in the presence of an acid and then said nitroxyl radical is added to this solution, to obtain a porous sol-gel polymeric oxide with a fractal macromolecular structure.

10. The process according to claim 2, wherein said reductive amination is carried out by stirring a solution of said 4-oxo-TEMPO in methanol with said 3-aminopropyl-trimethoxysilane, and reducing the thus formed imine with $NaBH_3CN$.

11. The process according to claim 8, wherein said nitroxyl radical is TEMPO or a compound that forms 2,2,6,6-tetramethyl-1-piperidinyloxy under the instant reaction conditions and said radical is physically entrapped within a sol-gel matrix adding a solution thereof in methanol to said compound following said one-step procedure.

12. The process according to claim 2, wherein said catalytic porous materials are in the shape of powders, films, monoliths, or fibers.

13. A process according to claim 3, wherein said liquid phase is an organic solvent, a biphasic organic solvent-water system, or water and said primary oxidant is NaOCl, NaOBr, $HNO_3$, $CuCl/O_2$, $K_3Fe(CN)_6$, or $NO_2$.

14. A process according to claim 3, wherein said alcohol substrate is an alkyl alcohol, an aryl alcohol, a steroid alcohol, an allylic alcohol, a terpenoid alcohol or retinol and it is oxidized in a bi-phasic reaction system $CH_2Cl_2$—$H_2O$, said primary oxidant is aqueous alkaline NaOCl and wherein said nitroxyl radical is 4-oxy-TEMPO and said monomer precursor is 3-aminopropyl-trimethoxysilane to obtain a catalytic material containing chemically linked radicals.

15. A process according to claim 3, wherein said alcohol substrate is a monomer or an oligomeric carbohydrate protected at the anomeric center, said solvent is water, said oxidant is alkaline NaOCl or NaOCl in the presence of a catalytic amount of NaBr, and wherein said nitroxyl radical is 4-oxy-2,2,6,6-tetramethyl-1-piperidinyloxy and said monomer precursor is 3-amino-propyl-trimethoxysilane to obtain a catalytic material containing chemically linked radicals.

16. A process according to claim 15, wherein said catalytic material is in the form of pumice stones coated with said sol-gel film doped with said nitroxyl radicals, and said carbohydrate is a water soluble polymer.

17. The process according to claim 3, wherein P is a non-hydrolyzable group.

18. A process according to claim 3, wherein said alcohol substrate is an alkyl alcohol, an aryl alcohol, a steroid alcohol, an allylic alcohol, a terpenoid alcohol or retinol and it is oxidated in a bi-phasic reaction system $CH_2Cl_2$—$H_2O$, wherein said primary oxidant is aqueous alkaline NaOCl, and wherein said nitroxyl radical is 4-oxy-2,2,6,6,-tetramethyl-1-piperidinyloxy and said compound that forms 2,2,6,6-tetramethyl-1-piperidinyloxy is 3-aminopropyl-trimethoxysilane to obtain a catalytic material containing chemically linked radicals, wherein said radical is tethered to said compound that forms 2,2,6,6-tetramethyl-1-piperidinyloxy through reductive amination by stirring for three hours a solution of 4-oxy-2,2,6,6,-tetramethyl-1-piperidinyloxy in methanol with a slight excess of 3-aminopropyl-trimethoxysilane, and reducing the thus formed imine with $NaBH_3CN$.

* * * * *